United States Patent
Wake et al.

(10) Patent No.: US 6,681,130 B2
(45) Date of Patent: Jan. 20, 2004

(54) METHOD FOR IMPROVING THE ACCURACY OF DATA OBTAINED IN A LASER IMAGING APPARATUS

(75) Inventors: Robert H. Wake, Cooper City, FL (US); William Dieckmann, Miami Beach, FL (US)

(73) Assignee: Imaging Diagnostic Systems, Inc., Plantation, FL (US)

( * ) Notice: Subject to any disclaimer, the term of this patent is extended or adjusted under 35 U.S.C. 154(b) by 125 days.

(21) Appl. No.: 10/097,121

(22) Filed: Mar. 14, 2002

(65) Prior Publication Data

US 2003/0176793 A1 Sep. 18, 2003

(51) Int. Cl.$^7$ .................................................. A61B 5/00
(52) U.S. Cl. ..................... 600/407; 600/473; 600/476; 356/435; 250/208.1; 250/214 A
(58) Field of Search ................................ 600/407, 476, 600/425, 473, 475, 477; 250/208.1, 214 R, 214 A, 214 AG, 214.1, 332, 334, 341.1; 356/215, 222, 343, 435

(56) References Cited

U.S. PATENT DOCUMENTS

| | | |
|---|---|---|
| 6,150,649 A | 11/2000 | Wake et al. |
| 6,331,700 B1 | 12/2001 | Wake et al. |
| 6,339,216 B1 | 1/2002 | Wake et al. |

*Primary Examiner*—Ruth S. Smith
(74) *Attorney, Agent, or Firm*—Shlesinger, Arkwright & Garvey LLP

(57) ABSTRACT

A method for collecting data for use in image reconstruction of an object being scanned, comprises providing a plurality of detectors disposed in an arc around the object being scanned to detect light passing through the object; impinging a laser beam at a point on the object; integrating the output of each detector at a number of successive time intervals, each time interval being longer than the previous time interval; digitizing the integrated output from each time interval; successively digitizing multiple times the integrated output from the longest time interval and averaging the results; orbiting the detectors and laser beam to another point on a circle; and repeating the above steps until a complete circle has been traversed.

12 Claims, 2 Drawing Sheets

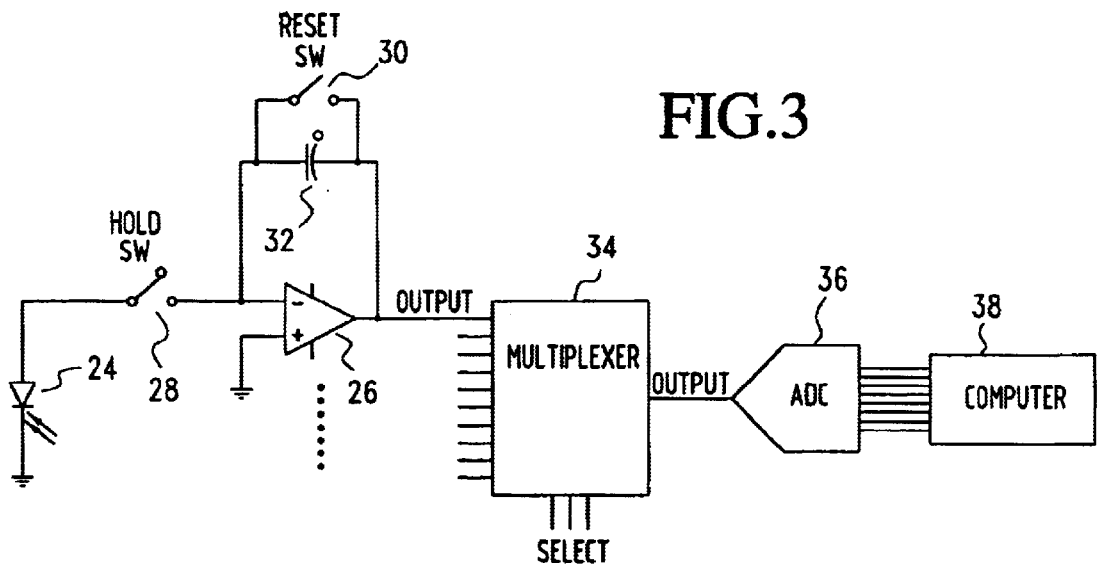
FIG.3
FIG.4
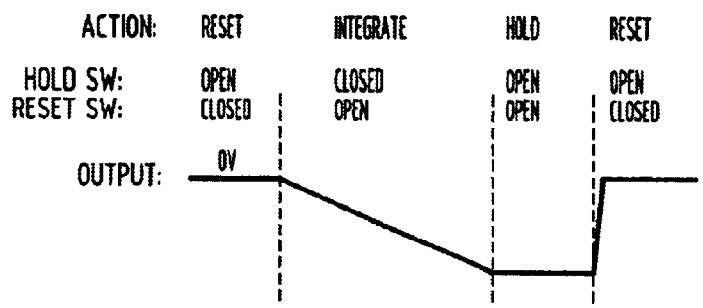
FIG.5
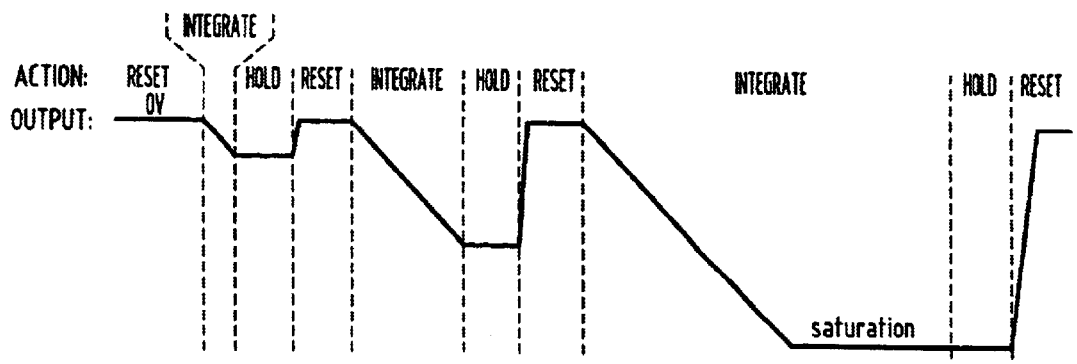

METHOD FOR IMPROVING THE ACCURACY OF DATA OBTAINED IN A LASER IMAGING APPARATUS

FIELD OF THE INVENTION

The present invention relates generally to a method for improving the accuracy of data obtained in a diagnostic medical imaging apparatus that employs a near-infrared laser as a radiation source and a detector array with variable gain amplifiers that can accommodate the wide dynamic range of signals available from each detectors.

OBJECTS AND SUMMARY OF THE INVENTION

It is an object of the present invention to provide a method for collecting data for use in image reconstruction of an object being scanned using an optical tomographic scanner where the method accommodates the large dynamic range of light levels that can vary as high as $10^7:1$.

It is another object of the present invention to provide a method for collecting data for use in image reconstruction of an object being scanned that provides for reducing the error when digitizing the signals generated by photodetectors in an optical tomographic scanner where the signals can range approximately 1 mV–10 V.

In summary, the present invention provides a method for collecting data for use in image reconstruction of an object being scanned, comprising providing a plurality of detectors disposed in an arc around the object being scanned to detect light passing through the object; impinging a laser beam at a point on the object; integrating the output of each detector at a number of successive time intervals, each time interval being longer than the previous time interval; digitizing the integrated output from each time interval; successively digitizing multiple times the integrated output from the longest time interval and averaging the results; orbiting the detectors and laser beam to another point on a circle; and repeating the above steps until a complete circle has been traversed.

The present invention also provides a method for obtaining data from a photodetector array used in image reconstruction where the light intensity impinging on the detectors has a large dynamic range, comprising integrating the output of each photodector in the array for at least two time intervals, each time interval being longer than the previous time interval; digitizing the integrated output of each detector; successively digitizing multiple times the integrated output of each detector at the longest time interval and averaging the results; and selecting the value of the digitized data from the longest time interval for those detectors that did not saturate.

These and other objectives of the present invention will become apparent from the following detailed description.

BRIEF DESCRIPTIONS OF THE DRAWINGS

FIG. 3 is a schematic block diagram of a signal processing circuit for a detector using a switched integrator.

FIG. 4 is a sequence of functions of the switched integrator of FIG. 3.

FIG. 5 is a sequence of functions of the switched integrator of FIG. 3 with successively longer integration intervals.

DETAILED DESCRIPTION OF THE INVENTION

Figure 1:
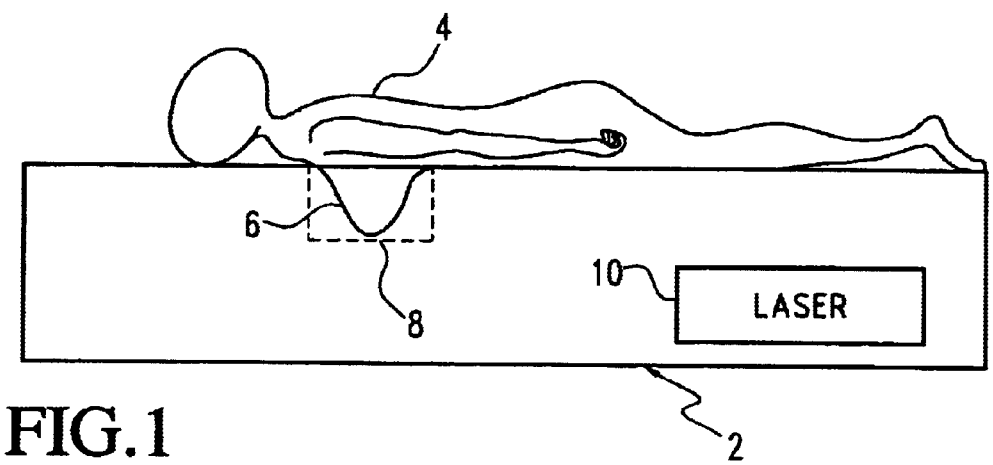
FIG. 1 is a schematic side elevational view of a laser imaging apparatus with a patient in prone position with one of her breast positioned within a scanner for an optical tomographic study.
Figure 2:
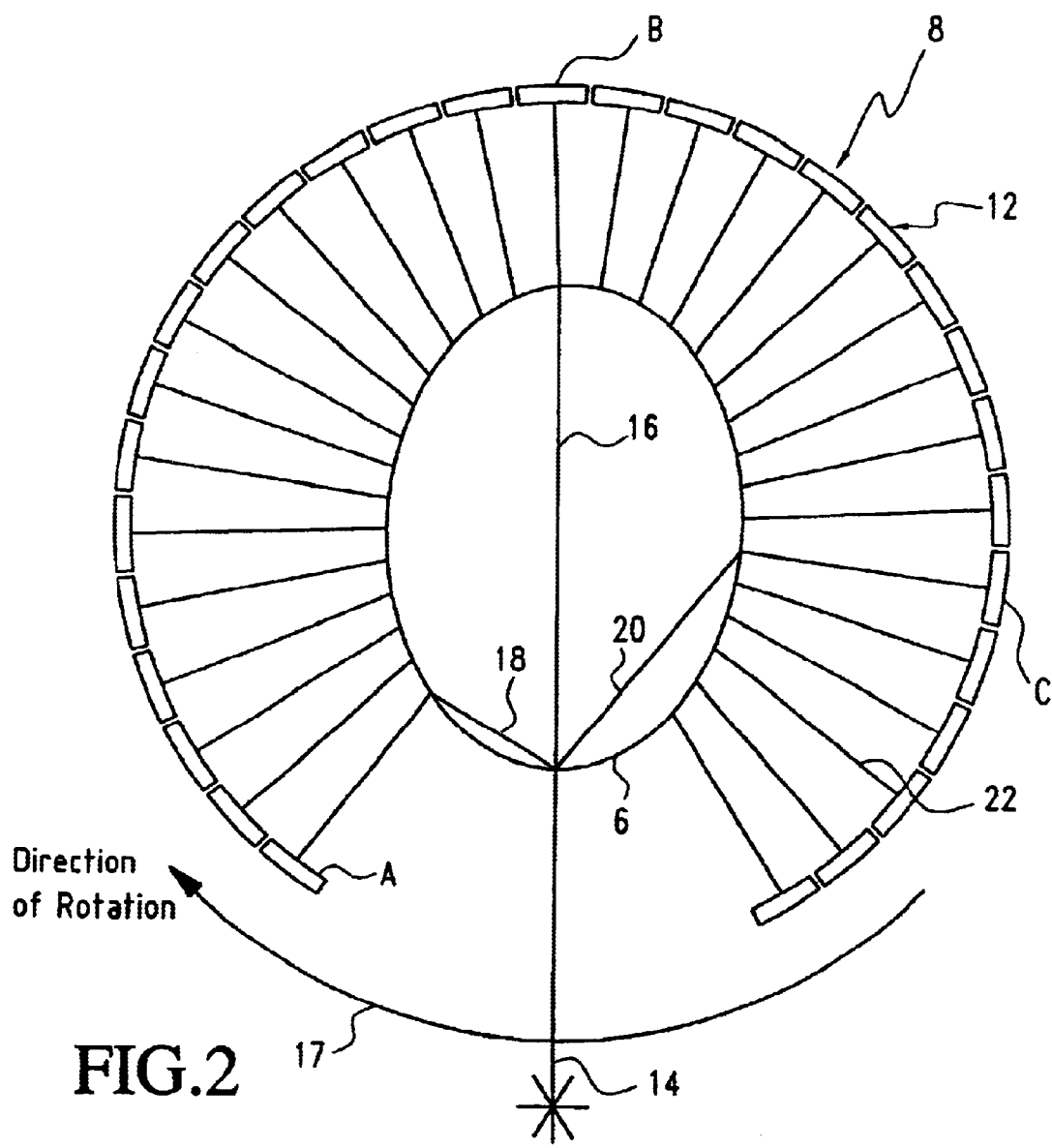
FIG. 2 is a schematic diagram of an optical scanner showing the breast disposed within an arc of detectors.

An optical tomographic scanning apparatus 2, such that disclosed in U.S. Pat. No. 5,692,511, is schematically shown in FIG. 1. A patient 4 is positioned prone on a top surface of the apparatus 2 with her breast 6 disposed pendant within an optical scanner 8. A laser beam from a laser source 10 is brought to the scanner 8 to illuminate the breast 6.

The optical scanner 8 comprises a detector ring 12 disposed around the breast in an arc. A laser beam 14 impinges on the breast 6. The laser beam traversing through the breast and exiting at the other side, as generally disclosed at 16, 18 or 20, is picked up by the respective detectors A, B and C. The laser beam 14 and the detector ring 12 are orbited around the breast for a complete circle in the direction generally indicated at 17. At each angular position in the orbit, light detected by the detector ring 12 is recorded for later use in reconstructing an image of the breast 6.

The laser beam 14, preferably a near-infrared laser, illuminates the breast and each detector sees light that is transmitted through a portion of the breast and re-emitted, such as for detectors A, B and C, for which light paths 18, 16 and 20 are shown for illustration purposes. Each detector has a restricted field of view whose axis is generally indicated at 22.

The dynamic range of light levels in the optical tomographic apparatus 2 is very large, which can range as high as $10^7:1$. The light levels are generally quite low and vary with detector position and scanned object size and composition. Between detectors A and B, for example, the light level may differ by a factor of $10^3$ to $10^5$. This is due to light absorption within the scanned object and the difference in path lengths for the light paths 18 and 16. The light transmission is given by:

$$I=I_0 e^{-\mu x}$$

where I is the detected intensity, $I_0$ is the incident intensity, $\mu$ is the effective linear attenuation coefficient of the medium (scanned object) and x is the path length in the medium. The ratios of intensities detected by detectors A and B is given by:

$$R=e^{-\mu(xB-xA)}$$

where R is the ratio intensities, xA is the path length in the medium for detector A and xB is the path length in the medium for detector B. For a $\mu=1.0$ cm$^{-1}$ which is a typical value for tissue and path lengths of xA=4 cm and xB=15 cm, the intensity ratio between these detectors is 60,000:1.

Different scanned objects or different breasts can exhibit attenuation values ranging 10:1 or greater. Changing position of the breast within the optical scanner will further exacerbate the dynamic range problem. The net effect is that the detectors are required to measure light intensities over a range of $10^7:1$ in the absolute worst case.

U.S. Pat. Nos. 6,150,649 and 6,331,700 disclose the use of integrating amplifiers with variable integration times as a partial solution to the dynamic range problem described above. Referring to FIG. 3, a signal processing block diagram for a detector 24 is shown. Each detector in the detector ring 12 preferably uses a silicon photodiode. Photodiodes advantageously exhibits small physical sizes and insentivity to acceleration and magnetic fields, unlike photomultiplier tubes. The quantum efficiency of photodiodes is advantageously far better than that of photomultipliers at the 800 nm near-infrared wavelength of biological interest. They are available with extremely small leakage currents for photoconductive application and high shunt resistances for photovoltaic application. In the optical scanning application, the photodiode photocurrents may be as low as a few picoamps ($10^{-12}$ Amps) to as high as 10 microamps.

Referring to FIG. 3, the photocurrent from photodiode 24 is impressed on the inverting input of an operational amplifier 26 if HOLD switch 28 is closed. If RESET switch 30 is open, the output of the operational amplifier 26 ramps negative, charging capacitor 32 at a rate given by:

$$V = \frac{i*t}{C}$$

where V is the output voltage, I is the photocurrent, t is the time that the photocurrent has been charging capacitor 24 and C is the value of capacitor 32. Thus, the circuit gain (Volts out per Amperes in) can be set by changing the capacitor or by changing the integration time.

Multiple integrating amplifiers are multiplexed into a single signal by a multiplexer 34. The analog signal is applied to the input of an analog-to-digital converter (ADC) 36 which digitizes the signal levels and supplies digital representation to a computer 38. For image reconstruction purposes, it should be understood that a plurality of photodiodes 24 that make up the detector ring 12 are each connected to a respective operational amplifier with its respective HOLD and RESET switches.

The function of the HOLD and RESET switches 28 and 30 and the resulting output voltages are shown in FIG. 4. Closing switch 30 causes the output level to go to zero. This is done immediately prior to making a measurement. Opening switch 30 and closing switch 28 causes the integrator to integrate the input current. Opening switch 28 causes the output voltage level to stop at its current value. This is done whenever the signal level is to be digitized. Closing switch 30 again resets the output back to zero preparatory to making another measurement.

Preferably, the output of each photodiode 24 is integrated at several different integration intervals, each one successively longer than the previous one and the value at the end of each integration interval is digitized. The last integration interval may be sufficiently long that the operational amplifier 18 saturates, which is harmless for the electronics. This may happen for photodetectors with short path lengths where the output signals are initially larger.

FIG. 5 illustrates the switched integrator behavior for three different integration intervals. Note that the second integration interval is longer than the first one and shorter than the third one. The third integration interval shows a saturation condition, in which case the output from the interval would not be used in image reconstruction.

The integration times could be fixed for the entire detector ring or could be different for each detector. The integration times could be several fixed values or could be adapted to the light levels present. In the preferred embodiment, there are six integration times, each four times the length of the previous one, covering an integration time range of 1024:1. For example, using a 100 millisecond integration interval as the largest integration interval, the one picoamp minimum photocurrent from the photodiode 24 produces an output signal of 1 millivolt. Using a 100 microsecond integration interval as the smallest integration interval, a 10 microamp maximum photocurrent produces an output signal of 10 volts, just within the maximum input range of the ADC 36.

In the preferred embodiment, the integrator uses one-half of a Burr-Brown ACF2101, which is a dual switched integrator. The multiplexer is a tree of 8:1 analog multiplexers. The ADC 36 is preferably a 14-bit ADC with an 800 nanosecond conversion time. The ACF2101 has an internal 100 pF feedback capacitor 32.

An external state machine controls the timing of the HOLD and RESET inputs to the operational amplifier 26 to effect the varied integration timing. This could be implemented in a variety of methods, all commonly known.

The present invention addresses the very low photocurrent domain of the dynamic range of a few picoamps. At one picoamp photocurrent, even a 100 millisecond integration interval produces a 1 millivolt output from the preferred electronics configuration. With the preferred 14-bit ADC, with the 10 volt full scale input range, 1 bit corresponds to 610 microvolts of input signal. Therefore, the 1 millivolt input signal is 1.6 bits. The quantization error is 60% of the signal. Switching to a 16 bit-ADC would still leave a 15% quantization error.

The quantization error looks like an additive noise source. It is additive to an otherwise quite good signal. With 1 picoamp charging the capacitor 32 for 100 milliseconds, $10^{-3}$ coulombs of charge are stored on capacitor 32. This charge is 625,000 electrons and the statistical uncertainty or "shot noise" is $1/(625,000)^{1/2}$ or ±0.12%. Thus, the signal stored on capacitor 32 is quite good, but the additive noise due to ADC quantization and any electrical noise is large. The typical additive electrical noise is at least 1 bit.

In accordance with the present invention, the signal is oversampled, that is, digitized repeatedly, when it is suspected that the signal might be small and susceptible to additive noise and quantization error. This would be the case for detectors with relatively long pathlengths. On the longest integration interval, (the sixth integration interval), the signal is digitized preferably 29 times consecutively. The computer 38, as part of the signal processing, averages the multiple samplings. The signal-to-noise ratio (SNR) improves by the square root of the number of samplings, assuming statistically independent measurements which is a good assumption. For a 29 times oversampling, the SNR will improve by a factor of approximately 5. This reduces the quantization error to 12% for the 14-bit ADC and 3% for the 16-bit ADC. Although 29 times oversampling is preferred, more or less oversampling can be used with corresponding benefit.

The 14-bit ADC has an SNR, therefore dynamic range, equivalent to 13 bits. The 1024:1 integration time range adds 10 bits to the dynamic range. The 29 times oversampling adds 2.3 bits to the dynamic range, for a total dynamic range of 25.3 bits or a dynamic range of $4.1 \times 10^7:1$, which exceeds the requirement.

The oversampling increases the overall measurement time, but the SNR improvement outweighs the minor time increase. In fact, the longest integration time can be decreased, relying on the oversampling to more than compensate for the SNR decrease that a shorter integration time would yield. A compromise would be to halve the longest integration time (therefore, the total scanning time) with the 29 times oversampling still yielding a factor of 2+ improvement in SNR versus no oversampling.

From each detector, six outputs are generated, one for each of the six integration intervals, and the largest data that does not saturate is selected for image reconstruction. Each of the selected data is then normalized at the various integration times so that all detectors are seen as if having been integrated at the same time interval.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A method for collecting data for use in image reconstruction of an object being scanned, comprising:
   a) providing a plurality of detectors disposed in an arc around the object being scanned to detect light passing through the object;
   b) impinging a laser beam at a point on the object;
   c) integrating the output of each detector at a number of successive time intervals, each time interval being longer than the previous time interval;
   d) digitizing the integrated output from each time interval;
   e) successively digitizing multiple times the integrated output from the longest time interval and averaging the results;
   f) orbiting the detectors and laser beam to another point on a circle; and
   h) repeating steps (b)–(e) until a complete circle has been traversed.

2. A method as in claim 1, wherein the number of successive time intervals is 6.

3. A method as in claim 2, wherein each time interval is 4 times the length of the preceding time interval.

4. A method as in claim 1, wherein the digitizing is implemented with a 14-bit analog-to-digital converter.

5. A method as in claim 1, wherein the digitizing is implemented with a 16-bit analog-to-digital converter.

6. A method as in claim 1, wherein the successively digitizing multiple times is 29 times.

7. A method for obtaining data from a photodetector array used in image reconstruction where the light intensity impinging on the detectors has a large dynamic range, comprising:
   a) integrating the output of each photodector in the array for at least two time intervals, each time interval being longer than the previous time interval;
   b) digitizing the integrated output of each detector;
   c) successively digitizing multiple times the integrated output of each detector at the longest time interval and averaging the results; and
   d) selecting the value of the digitized data from the longest time interval for those detectors that did not saturate.

8. A method as in claim 7, wherein the at least two time intervals is 6.

9. A method as in claim 8, wherein each time interval is 4 times the length of the preceding time interval.

10. A method as in claim 7, wherein the digitizing is implemented with a 14-bit analog-to-digital converter.

11. A method as in claim 7, wherein the digitizing is implemented with a 16-bit analog-to-digital converter.

12. A method as in claim 7, wherein the successively digitizing multiple times is 29 times.

* * * * *